United States Patent
Pinion et al.

(10) Patent No.: US 11,950,811 B2
(45) Date of Patent: Apr. 9, 2024

(54) OCCIPITAL PLATES AND RELATED METHODS

(71) Applicant: Alphatec Spine, Inc., Carlsbad, CA (US)

(72) Inventors: Catherine Pinion, San Diego, CA (US); Fernando Olea, Escondido, CA (US); Thomas Henry Hackathorn, II, Encinitas, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 401 days.

(21) Appl. No.: 17/479,884

(22) Filed: Sep. 20, 2021

(65) Prior Publication Data
US 2022/0087722 A1 Mar. 24, 2022

Related U.S. Application Data

(60) Provisional application No. 63/081,631, filed on Sep. 22, 2020.

(51) Int. Cl.
*A61B 17/70* (2006.01)

(52) U.S. Cl.
CPC ...... *A61B 17/7055* (2013.01); *A61B 17/7032* (2013.01); *A61B 17/7059* (2013.01)

(58) Field of Classification Search
CPC ............ A61B 17/7059; A61B 17/7053; A61B 17/7055; A61B 17/7058; A61B 17/7061; A61B 17/705; A61B 17/7032; A61B 17/7002; A61B 17/7035; A61B 17/7041; A61B 17/7043; A61B 17/7046; A61B 17/7047; A61B 17/7049

See application file for complete search history.

(56) References Cited

U.S. PATENT DOCUMENTS

| | | | |
|---|---|---|---|
| 6,524,315 B1 | 2/2003 | Selvitelli |
| 6,547,790 B2 | 4/2003 | Harkey |
| 6,902,565 B2 | 6/2005 | Berger |
| 7,303,563 B2 | 12/2007 | Poyner |
| 7,572,282 B2 | 8/2009 | Boomer |
| 7,575,588 B2 | 8/2009 | Barker |

(Continued)

FOREIGN PATENT DOCUMENTS

| | | |
|---|---|---|
| EP | 3366240 A1 | 8/2018 |
| WO | 2004/069038 A2 | 8/2004 |

(Continued)

OTHER PUBLICATIONS

International Preliminary Report on Patentability, International Application No. PCT/US2021/051224, dated Apr. 6, 2023.

*Primary Examiner* — Samuel S Hanna
(74) *Attorney, Agent, or Firm* — Robert Winn

(57) ABSTRACT

Disclosed herein are occipital plates that include a fixation plate portion and at least two extensions integrally connected to the fixation plate portion and extending away from the fixation plate portion. The fixation plate portion has a plurality of through-holes for receiving bone screws that secure the occipital plate to a patient's skull or, specifically, the occiput. Each extension includes a slot for removably receiving a rod connector or a rod-to-rod connector, the slots having an entry area or portion for receiving a connector and a holding area or portion for maintaining the connector in the slot.

16 Claims, 7 Drawing Sheets

(56) References Cited

U.S. PATENT DOCUMENTS

| | | |
|---|---|---|
| 7,901,433 B2 | 3/2011 | Forton |
| 8,007,499 B2 | 8/2011 | Piehl |
| 8,187,277 B2 | 5/2012 | Paul |
| 8,246,662 B2 | 8/2012 | Lemoine |
| 8,506,567 B2 | 8/2013 | Ziemek |
| 8,636,737 B2 | 1/2014 | Lemoine |
| 8,728,080 B2 | 5/2014 | Boomer |
| 8,740,953 B2 | 6/2014 | Hoffman |
| 8,900,276 B2 | 12/2014 | Purcell |
| 8,940,023 B2 | 1/2015 | Hawkins |
| 9,387,013 B1 | 7/2016 | Shoshtaev |
| 9,439,687 B2 | 9/2016 | Lemoine |
| 9,763,704 B2 | 9/2017 | Hawkins |
| 9,877,746 B2 | 1/2018 | Hawkins |
| 9,956,009 B1 | 5/2018 | Shoshtaev |
| 10,368,918 B2 | 8/2019 | Shoshtaev |
| 2005/0124994 A1 | 6/2005 | Berger |
| 2005/0240181 A1 | 10/2005 | Boomer |
| 2006/0155283 A1 | 7/2006 | Doherty |
| 2006/0155284 A1 | 7/2006 | Doherty |
| 2008/0147123 A1 | 6/2008 | Shermerhorn |
| 2008/0177314 A1 | 7/2008 | Lemoine |
| 2009/0043341 A1 | 2/2009 | Tyber et al. |
| 2009/0125067 A1 | 5/2009 | Mazzuca |
| 2009/0312801 A1 | 12/2009 | Lemoine |
| 2010/0222779 A1* | 9/2010 | Ziemek ............ A61B 17/7055 606/71 |
| 2010/0222825 A1 | 9/2010 | Paul |
| 2011/0106085 A1 | 5/2011 | Null |
| 2013/0197641 A1 | 8/2013 | Shepard et al. |
| 2017/0035465 A1 | 2/2017 | Robinson et al. |
| 2018/0140335 A1 | 5/2018 | Hawkins |

FOREIGN PATENT DOCUMENTS

| | | |
|---|---|---|
| WO | 2006/009794 A1 | 1/2006 |
| WO | 2006/073646 A1 | 7/2006 |
| WO | 2007/005561 A2 | 1/2007 |
| WO | 2008/016955 A2 | 2/2008 |
| WO | 2008/042633 A2 | 4/2008 |
| WO | 2008/082814 A1 | 7/2008 |
| WO | 2009/055747 A1 | 4/2009 |
| WO | 2009/061604 A1 | 5/2009 |

* cited by examiner

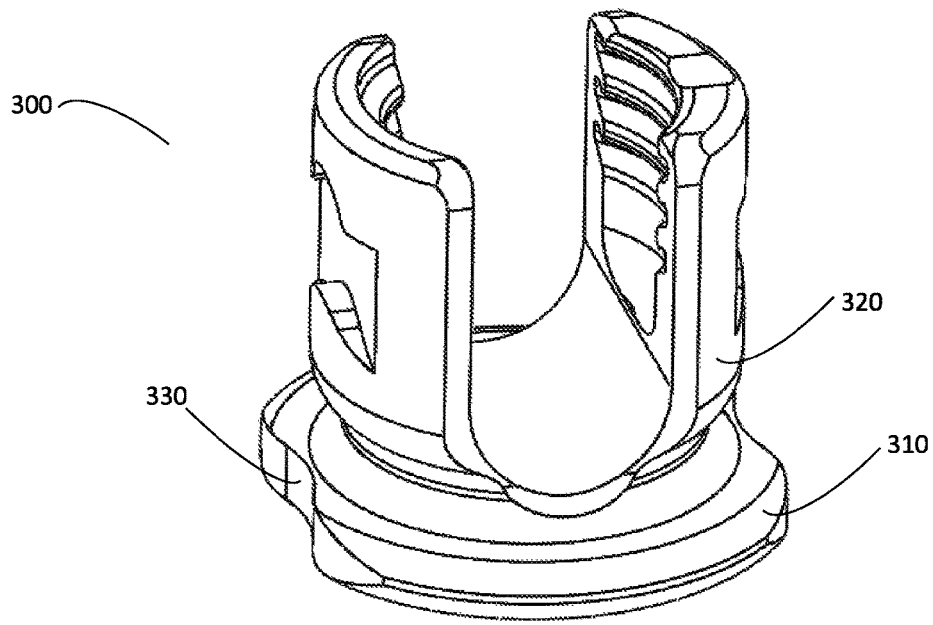
FIG. 9A
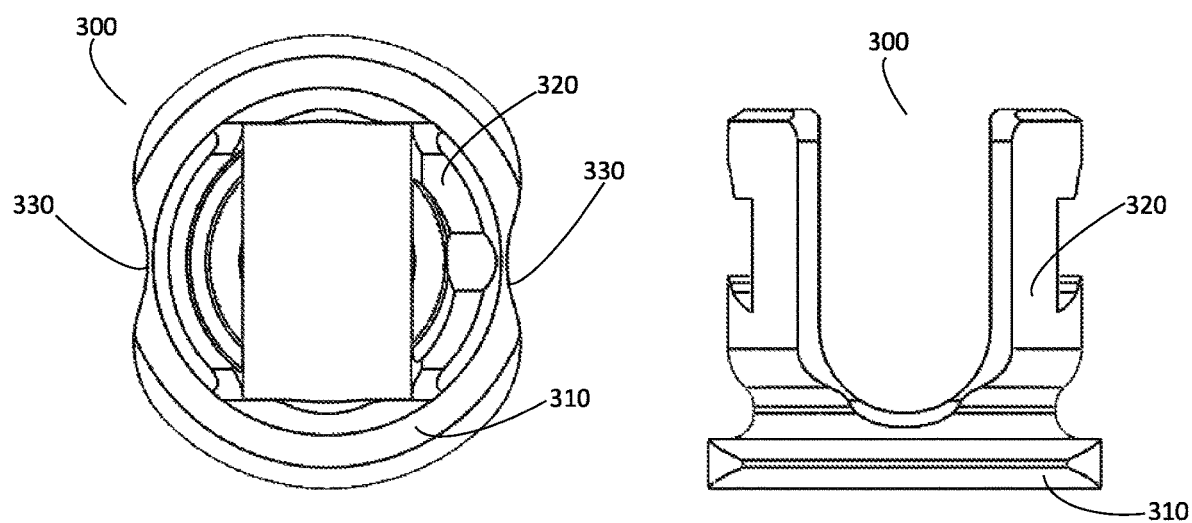
FIG. 9B
FIG. 9C

OCCIPITAL PLATES AND RELATED METHODS

RELATED APPLICATIONS

The present application claims priority to U.S. Provisional Application No. 63/081,631, filed Sep. 22, 2020, the entire contents of which are incorporated herein by reference.

FIELD OF THE INVENTION

The present invention relates generally to the field of surgery, and more specifically, to an adjustable occipital plate which may be used in conjunction with a posterior rod system to fixate the occipital/cervical junction between the cranium and the spine.

BACKGROUND

Occipital-cervical fixation has been achieved using a variety of techniques which generally provide stabilization of the base of the skull with respect to the neck. In order to promote fusion, for example, bone struts formed of autogenous ribs or curved iliac crest struts have been fixed to the occiput and spinous processes, cervical laminae, or facets. Wires are used to fix the struts in place until bone fusion occurs.

The thickness of the occiput varies, however, and thus, the occiput is typically wired in regions of greater thickness such as near the foramen magnum, at the nuchal line, and along the midline crest. Holes are drilled in the occiput to receive the wires that are also fed through holes in the struts. Although bone fusion occurs with this technique, the struts may be weak prior to fusion, and additional orthosis is applied such as with a halo vest or other hard collar until the struts can provide acceptably strong immobilization. Alternatively, metal struts maybe used.

Other techniques for occipital-cervical fixation involve the use of other metal implants. One metal implant is a stainless steel, U-shaped device known as a Steiuman pin. The threaded pin is bent to match the contour of the occipital-cervical region, and fixed to the occiput and cervical laminae or facets using wires. The pin is generally symmetrically disposed about the spine, with the sides of the "U" creating a central region in which a bone graft can be disposed and further wired to the pin. When attached to the occiput and spine, the pin assumes an inverted-U configuration. Several holes are formed in the occiput so that the U-bend may be fixed in place.

Additional metal implants include grooved or roughened titanium rods, smooth steel rods in the form of a Hartshill rectangle or Ransford loop, a Cotrel-Dubousset rod screw plate, and titanium frames have been employed.

SUMMARY

Disclosed herein are occipital plates that include a fixation plate portion and at least two extensions integrally connected to the fixation plate portion and extending away from the fixation plate portion. The base portion has a plurality of through-holes for receiving bone screws that secure the occipital plate to a patient's skull or, specifically, the occiput.

Each extension includes a slot for receiving a rod connector or a rod-to-rod connector, the slots having an entry area or portion for receiving a connector and a holding area or portion for maintaining the connector in the slot. The connectors are removably inserted into the slots on the extensions, the holding area of the slots having a flange around at least a portion of the slots' perimeters to hold the connectors in the slots. The slots also include a flexible tab that is depressed to allow the connectors to be inserted into the slots. The flexible tab has an extension or projection that prevents the connector from unintentionally being removed from the slot.

Each connector has a base with a protruding edge configured to be received in the slot and held in place by the flange on the slot. The connectors further have at least two vertical walls forming a U-shaped opening configured to receive a fixation rod. The rod-to-rod connectors have at least three vertical walls so as to form two U-shaped openings for receiving two fixation rods. In some embodiments, the rod-to-rod connectors have four vertical walls.

In some embodiments, the plurality of through-holes includes at least three midline through-holes—a superior through-hole, a middle through-hole, and an inferior through-hole—positioned along a first imaginary line running from the superior end to the inferior end of the fixation plate portion. The first imaginary line may be located substantially in the middle of the fixation plate portion. In some embodiments, the plurality of through-holes further includes at least two horizontal through-holes, each one positioned on either side of the midline through-holes.

In some embodiments, each of the two extensions extends in a direction substantially perpendicular to the first imaginary line of the fixation plate portion. In some embodiments, the two extensions extend at an angle relative to the first imaginary line of the fixation plate portion, which angle may be greater than about 90°, greater than about 95°, greater than about 100°, greater than about 105°, or greater than about 110°.

Each slot defines a second imaginary line that intersects the first imaginary line. In some embodiments, the point of intersection is at about the inferior through-hole, at about the middle through-hole, at about a point between the respective centers of the middle and inferior through-holes, or at a point inferior to the center of the inferior through-hole.

In some embodiments, the flex tab comprises an arm having a proximal end secured to the extension and a distal end that is able to be deflected. The distal end of the arm may include a retaining protrusion configured to prevent a rod connector base from sliding out of the slot. In some embodiments, the protrusion is located at a point near an edge of the entry portion of the slot such that the connector need be moved only partially into the holding portion for the protrusion and flex tab to return to their normal position. In some embodiments, the protrusion is located further away from the edge of the entry portion so as to require the connector to be moved further into the holding portion before the flex tab returns to its normal position.

In some embodiments, the occipital plate includes bend zones positioned between the fixation plate portion and the extensions and/or between the middle through-hole and inferior through-hole. In some embodiments, there are one or two bend zones running from the superior end to the inferior end of the fixation plate on either side of the midline through-holes.

In some embodiments, the base of the rod connector is cylindrical in shape so as to be able to rotate within the slot. In some embodiments, the base has at least one straight edge so as to either resist or prevent rotation of the connector. The rod connectors may be configured to receive a single stabilization rod or two stabilization rods. If configured to receive two stabilization rods, such a connector may have three walls or four walls to form two U-shaped openings, which openings may be parallel or offset and may be positioned side-by-side at the same or a different level from each other or offset from each other at the same or a different level.

Also disclosed herein are occipital plate systems that include an occipital plate as disclosed herein, a plurality of bone or fixation screws, and two or more fixation rods received in the U-shaped openings of the rod connectors. The fixation screws have a threaded shank and a head, the head having a larger diameter than the threaded shank, and at least a portion of the head having a larger diameter than the diameter of at least a portion of the through-holes.

The present disclosure also relates to methods of implanting an occipital plate according to the present disclosure. Such methods include positioning the plate on the occiput of a patient's cranium, inserting a fixation screw through each through-hole of the occipital plate and into the cranium, inserting each rod connector into respective slots, positioning each rod connector as desired, placing one or more rods in each rod connector, and placing set screws in each rod connector to secure each of the rods in place as well as secure each rod connector in place in each slot.

These and other features are disclosed in greater detail in the accompanying figures and the Detailed Description below.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIGS. 9A-9C illustrate various views of an embodiment of a rod connector according to the present disclosure.

DETAILED DESCRIPTION

Disclosed herein are various embodiments of occipital plates and methods of using the same. Occipital plates are configured for implantation at the base of a patient's skull, i.e., the occiput, near where the patient's cervical spine meets the skull. In some spinal procedures where stabilization of the cervical spine is desired, there will be stabilization rods running along the cervical spine. In some cases, a surgeon may desire additional stability by securing the stabilization rods to the patient's skull; however, the angle of the rods along the cervical spine make it difficult to attach the rods to traditional plates secured to the occiput of the skull. To address this challenge, various rod designs, such as curved rods or hinged rods, have been developed to ameliorate the difference in angle between the cervical spine and the occiput.

The occipital plates disclosed herein address these challenges by achieving greater flexibility in securing stabilization rods to the skull. Such flexibility may be achieved by using rod connectors on the occipital plate that are variable in both angle and lateral orientation relative to the plate. Moreover, one or more rod-to-rod connectors may be used in lieu of simple single rod connectors so as to allow for three or four rods to be secured to the occipital plate. The plate itself may also provide greater flexibility and customization by including one or more bend zones in the plate. Such bend zones may be positioned between various through-holes so as to allow the plate to be shaped to a patient's skull shape. Such bend zones may also or alternatively be positioned between the through-holes and extensions on the plate where the rod connectors are found so as to further accommodate the angle and orientation of the stabilization rods.

The occipital plates of this disclosure further include the ability to install and/or remove rod connectors from the plate either ex situ or in situ. This feature allows not only for customization of the occipital plate to a surgeon's needs but also the ability to make changes during surgery.

Figure 1:
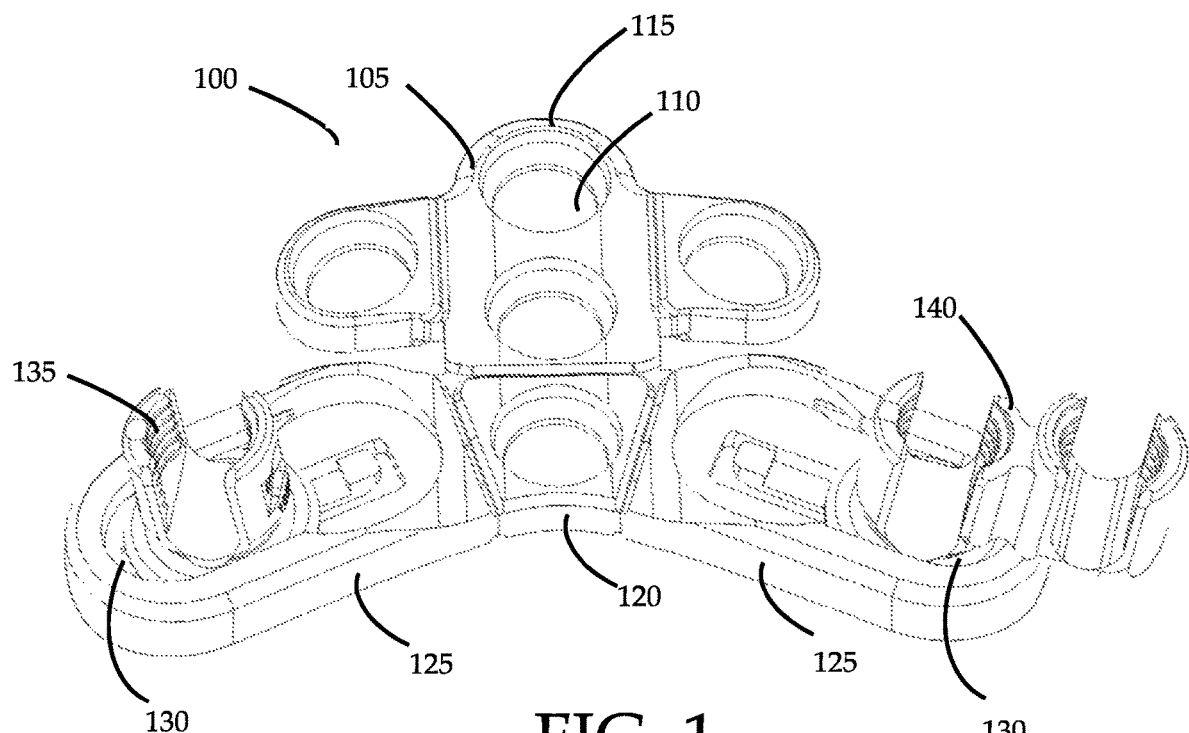
FIG. 1 is a perspective view of an exemplary occipital plate according to the present disclosure.

FIG. 1 illustrates an occipital plate 100 that includes a fixation plate portion 105 that, in this illustrated embodiment, includes five through-holes 110, three medial through-holes and two lateral through-holes. Each through-hole 110 is configured to receive a bone screw (not illustrated). Fixation plate portion 105 has a superior end 115 and an inferior end 120. Plate 100 includes two extensions 125 positioned toward the inferior end 120 of the fixation plate portion 105. As will be discussed in greater detail below, different embodiments of plate 100 will have the extensions 125 positioned at different points on fixation plate 105.

FIG. 1 also illustrates that each extension 125 includes a slot 130 configured to receive a rod connector. In some embodiments, the rod connector is a single rod connector 135 or a rod-to-rod connector 140. Rod connector 135 may be used in both slots 130. Rod-to-rod connector 140 may be used in both slots 130. In some embodiments, one slot will have one type of rod connector and the other slot will have the other type of rod connector. In other embodiments, only one rod connector (either single rod connector 135 or rod-to-rod connector 140) may be used.

Figure 2:
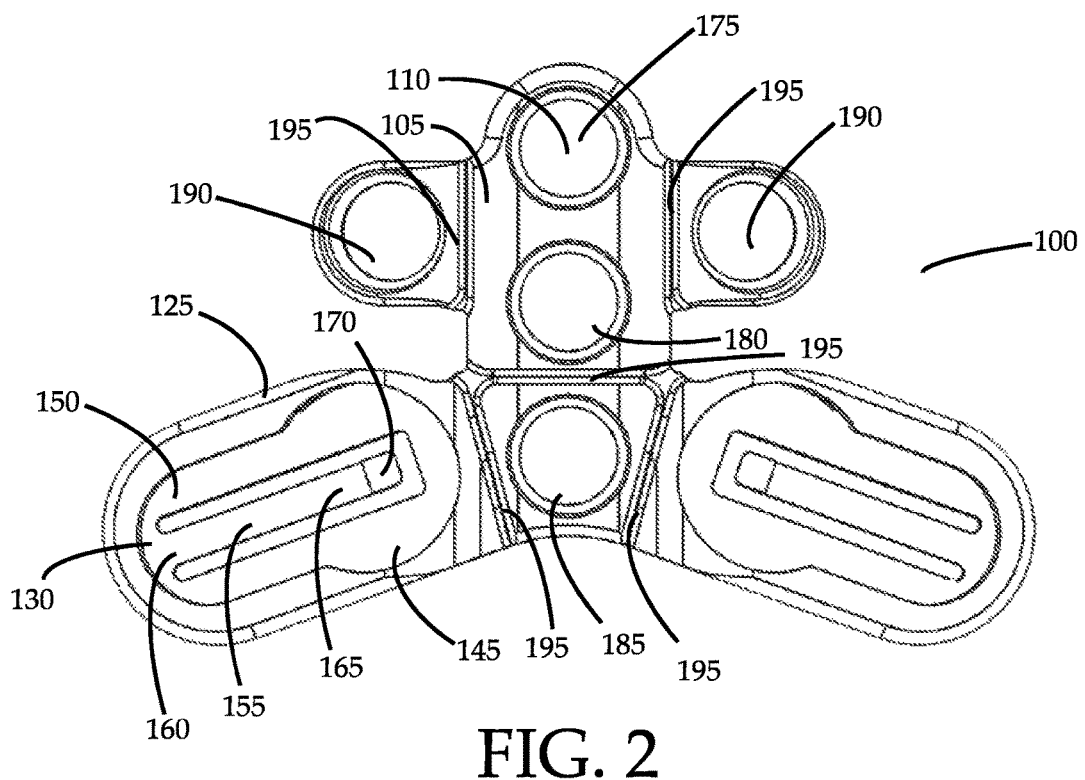
FIG. 2 is a top view of the occipital plate of FIG. 1 but not containing any rod connectors.

FIG. 2 illustrates that each extension 125 is an elongated member extending from fixation plate portion 105. Slot 130 runs much of the length of extension 125 and includes an entry portion 145 and a holding portion 150. Holding portion 150 is defined as having a lip or flange (discussed in greater detail below) configured to hold a flange of the rod connector. Entry portion 145 is defined as lacking the lip or flange of holding portion 150 so as to allow for the flange of the rod connector to pass, i.e., when installing the rod connector in extension 125 or removing the rod connector from extension 125. To this end, slot 130 further includes a flex tab 155 that includes a proximal portion 160 integrally formed with extension 125 and a distal portion 165 that includes a raised protrusion 170.

Figure 7A:
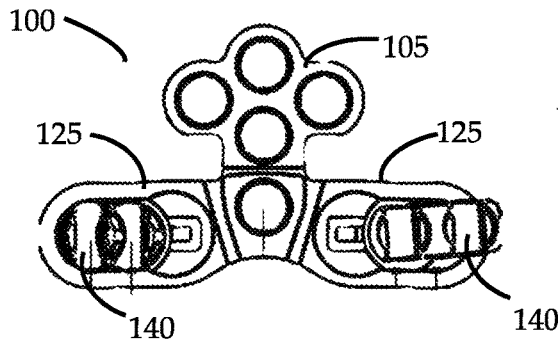
FIGS. 7A-7C illustrate various configurations of an occipital plate according to the present disclosure.
Figure 7B:
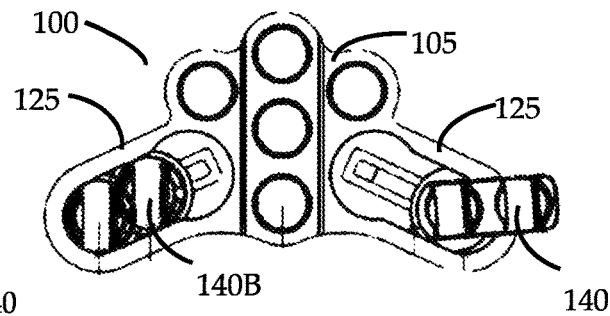
Figure 7C:
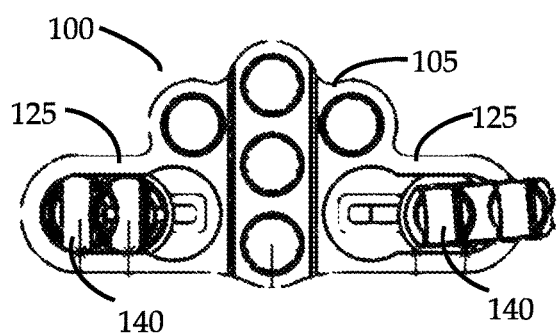

In this illustrated embodiment, slot 130 defines an imaginary line that lies at an angle to an imaginary line that is orthogonal to an imaginary line running from superior end 115 to inferior end 120. The angle can be any value between and including about −20° and about 60°. In some embodiments, the angle is about 0° to about 20°, about 10° to about 30°, or about 20° to about 40°. In the illustrated embodiment, the imaginary line of slot 130 intersects the imaginary line running from superior end 115 to inferior end 120 at a point on or about through-hole 185. In some embodiments, the point of intersection is superior to through-hole 185. In some embodiments, the point of intersection is inferior to through-hole 185. FIGS. 7A-7C illustrate variations on occipital plate 100 where the angle and position of extensions 125 is varied.

FIG. 2 additionally illustrates that through-holes 110 include both medial and lateral through-holes. The medial through-holes include superior through-hole 175, middle through-hole 180, and inferior through-hole 185. The medial through-holes are positioned along a medial line of plate 100, though in some embodiments, they may be positioned along a non-medial line and/or not along any line at all. Fixation plate portion 105 further includes lateral through-hole(s) 190, which may be positioned so that an imaginary line between the respective centers of lateral through-holes 190 sits roughly between superior through-hole 175 and middle through-hole 180. In some embodiments, lateral through-holes are positioned more toward superior end 115. In some embodiments, lateral through-holes are positioned more toward inferior end 120.

In the illustrated embodiment each through-hole 110 includes a larger diameter and a smaller diameter, the smaller diameter sitting beneath a top surface of fixation plate portion 105. In some embodiments, the smaller diameter portion of each through-hole 110 includes threads that threadingly engage threads on the fixation screw that is inserted into through-hole 110 and secured in place.

Also illustrated in FIG. 2 are multiple bend zones 195, three on fixation plate portion 105 and one at each connection point between fixation plate 105 and each extension 125. Some embodiments include more bend zones, and some embodiments include fewer bend zones or no bend zones. In some embodiments, the bend zones are located in different positions than those shown in FIG. 2 and/or are different lengths. Although the illustrated bend zones are each linear, some embodiments may include one or more bend zones that are not linear.

Figure 3:
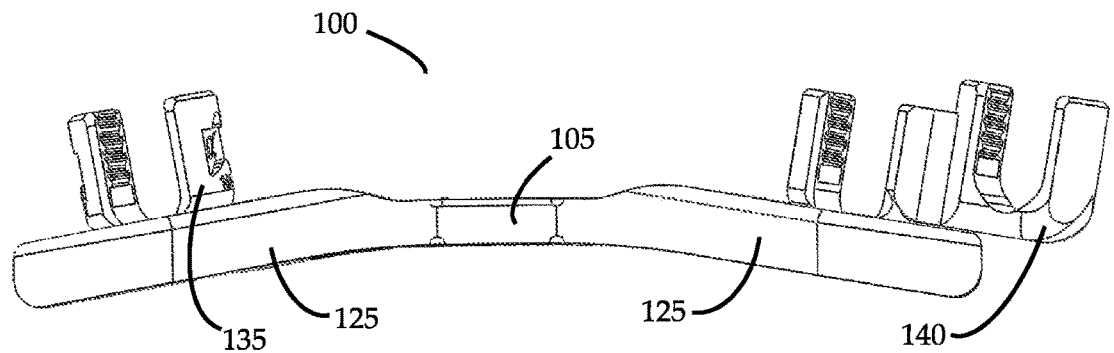
FIG. 3 is an elevation view from the inferior side of the occipital plate of FIG. 1.

FIG. 3 illustrates plate 100 in an elevation view from the inferior end. This perspective illustrates the bend achieved between extensions 125 and fixation plate portion 105. The bend or curvature of plate 100 may further be customized to meet patient and/or surgeon needs by utilizing bend zones 195 illustrated in FIG. 2. Even though FIG. 3 illustrates plate 100 with just one rod-to-rod connector 140, a skilled artisan would appreciate from this view that width greater than the plate's width can be achieved by utilizing two rod-to-rod connectors 140 with each one positioned at the most lateral position of slot 130.

Figure 4:
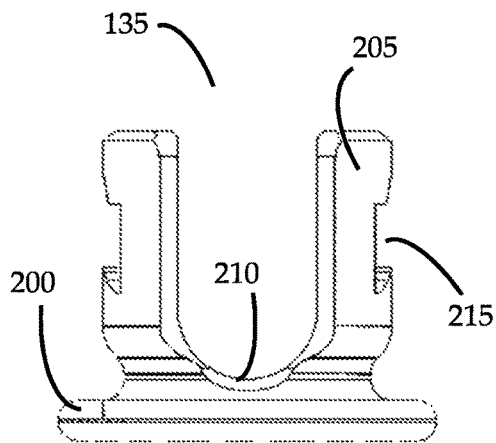
FIG. 4 is an elevation view of a rod connector configured for use with an occipital plate according to the present disclosure.

FIG. 4 illustrates an exemplary configuration of a rod connector 135, which includes a base portion 200 and a body portion 205 that comprises two vertical side walls that are threaded on their respective interior surfaces. The two walls form a U-shaped channel 210 configured to receive a fixation or stabilization rod (not illustrated). With a stabilization rod seated in channel 210, a set screw (not illustrated) can be secured to rod connector 135 by rotating the set screw so that its threads will mate with the threads on the side walls of body portion 205. Each side wall of body portion 205 may include a connection feature 215 to facilitate the insertion of rod connector 135 into entry portion 145 of slot 130, the removal of rod connector 135 from entry portion 145 of slot 130, the insertion of a rod into rod connector 135, and/or the insertion or removal of a set screw.

Base portion 200 is illustrated as being circular in shape and having a thickness chosen to allow base portion 200 to enter entry portion 145 of slot 130 and slide along slot 130 while not allowing toggle between rod connector 135 and extension 125. One advantage of being circular is that base portion 200 allows rod connector 135 to be rotated freely relative to occipital plate 100 so as to achieve the best orientation relative to any stabilization rods that will be secured to occipital plate 100 via rod connector 135. In some embodiments, base portion 200 is not circular but rather includes one or more straight edges that allow base portion 200 to slide along slot 130 but not rotate freely. Such a configuration may provide greater stability to fixation system, which includes occipital plate 100 and any connected stabilization rods.

FIG. 4 illustrates the side walls of body portion 205 as being substantially parallel and vertical relative to the plane of base portion 200. In some embodiments, the side walls may be angled relative to the plane of base portion 200, though the side walls will generally still be parallel.

According to some embodiments, base portion 200 includes one or more straight edges or indentations that run substantially parallel to one or both of the side walls of body portion 205, though a non-parallel configuration is possible in some embodiments. Such a configuration may allow two single rod connectors 135 to be used in a single slot 130 of plate 100. Although not always necessary to fit two single rod connectors 135 in a single slot 130, the inclusion of one or more straight edges on one or both single rod connectors 135 may allow for the single rod connectors 135 to be more closely positioned together. This possible feature is discussed in greater detail below with respect to FIGS. 9A-10B.

Figure 5A:
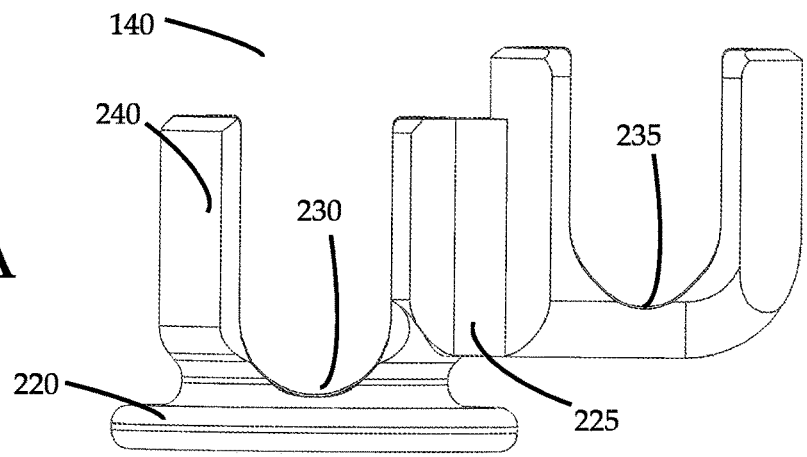
FIG. 5A is an elevation view of a rod-to-rod connector configured for use with an occipital plate according to the present disclosure.

FIG. 5A illustrates an exemplary configuration of a rod-to-rod connector 140, which includes not only a base portion 220, similar to rod connector 135, but rod-to-rod connector 140 further includes a body portion 225 that instead of having two vertical side walls has essentially four vertical side walls with two of the walls joined toward the middle of rod-to-rod connector 140. Similar to rod connector 135, rod-to-rod connector 140 includes a U-shaped channel 230, but rod-to-rod connector 140 further includes a second U-shaped channel 235. FIG. 5A illustrates the channel 235 is elevated relative to channel 230. In some embodiments, this elevation or difference in height between the channels may be greater or lesser, or there may be no elevation or difference in height between the channels, depending on the clinical need and/or surgeon preference.

Channel 230 and/or channel 235 may be configured to hold a stabilization rod in substantial alignment with the axis of each channel. Alternatively, one or both channels may be designed to allow the axis of the stabilization rod to deviate from the axis of the channel. For example, FIG. 5A illustrates that channel 235 exhibits a slight curvature toward the middle so as to allow a stabilization rod to be secured therein even if the rod's axis is not substantially parallel to the axis of channel 235.

Channel 230 and channel 235 are joined by a central wall. In some embodiments each channel may have its own set of side walls, such that body portion 225 comprises at least four side walls for the two channels. Such a configuration may be desirable if channel 230 and channel 235 are not in alignment, meaning that the middle of one channel is not aligned with the middle of the other channel so as to achieve a staggered arrangement (as illustrated in FIG. 7B as rod-to-rod connector 140B). Separate walls may also be desirable if the distance between channel 230 and channel 235 is to be increased.

Figure 5B:
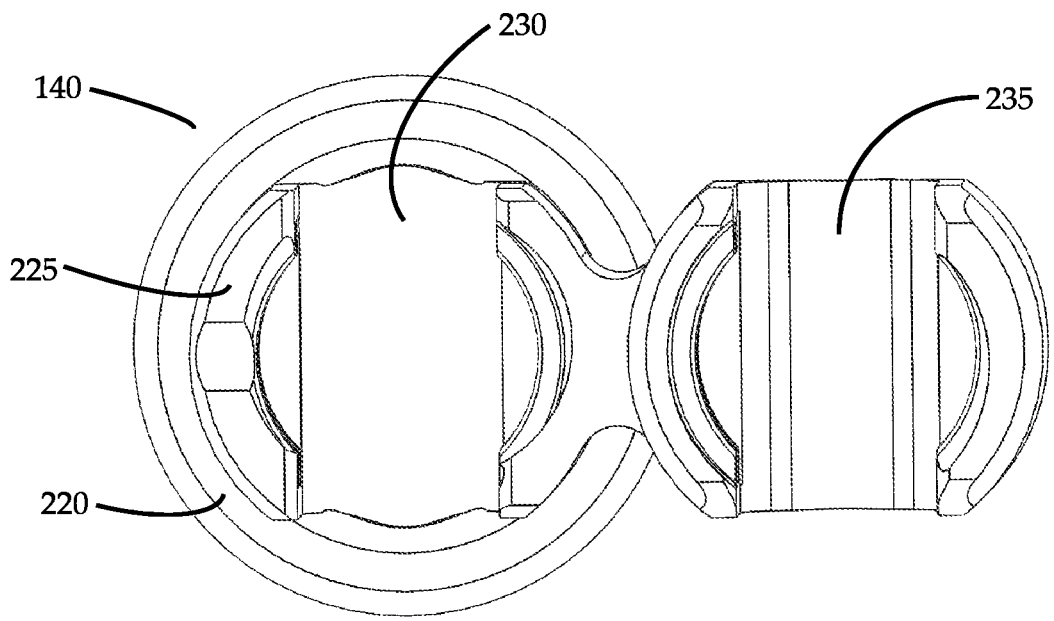
FIG. 5B is a top view of the rod-to-rod connector of FIG. 5A.

FIG. 5B illustrates that base portion 220 is circular, which like base portion 200, allows rod-to-rod connector 140 to rotate freely in slot 130. Not only does this allow for greater adjustment and customization of the overall construct, but for rod-to-rod connector 140, this also allows the position of channel 235 to be switched from one side of channel 230 to the other.

FIG. 5B also illustrates that channel 230 and channel 235 are substantially parallel, meaning that each channel defines an axis and that the two axes are substantially parallel. In some embodiments, the two axes are not substantially parallel. In addition to being substantially parallel, the two channels are substantially aligned (meaning the middle of one is lined up with the middle of the other) and are substantially equal in length. In some embodiments, the length of one or both channels can be longer or shorter depending on surgeon preference or patient need.

Figure 6A:
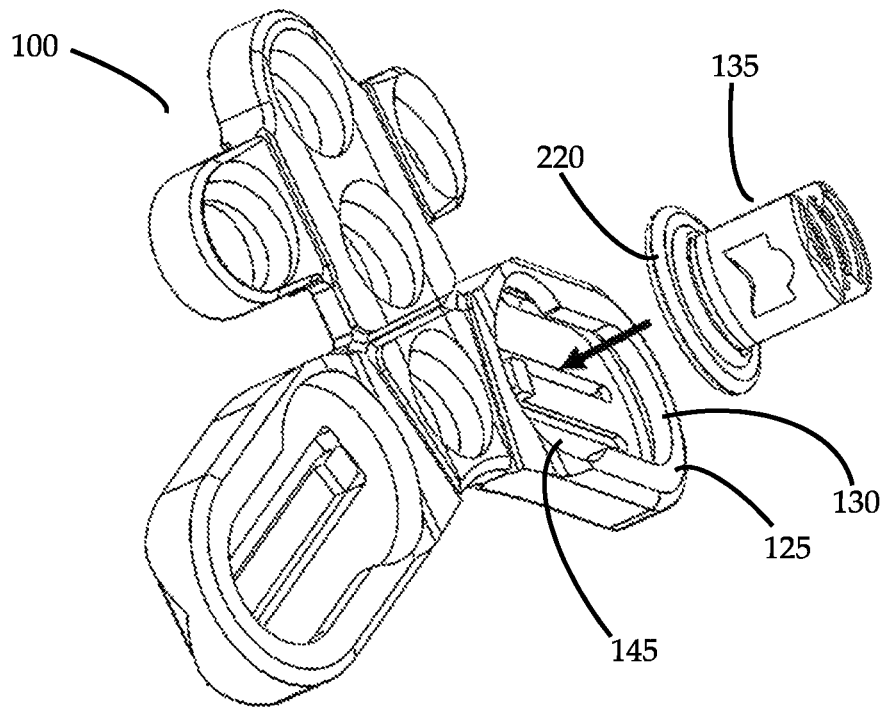
FIG. 6A is a perspective view illustrating how to insert a rod connector into an occipital plate according to the present disclosure.
Figure 6B:
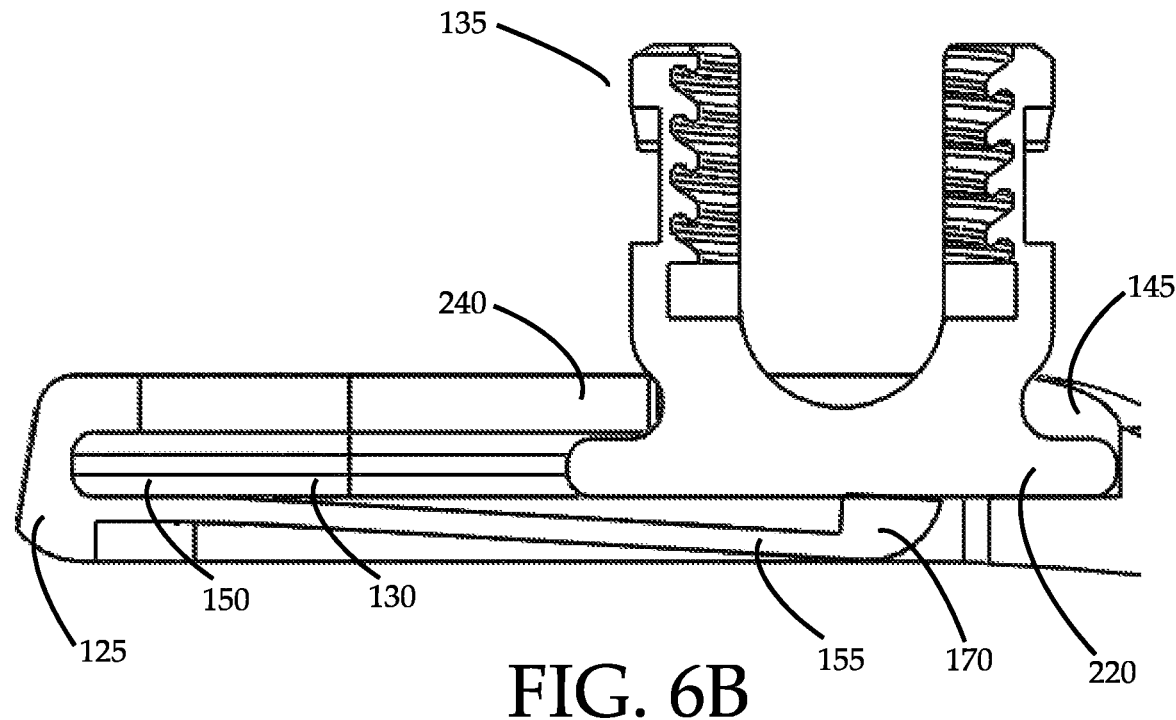
FIG. 6B is a section view illustrating how to deflect a flex tab while inserting a rod connector into an occipital plate according to the present disclosure.
Figure 6C:
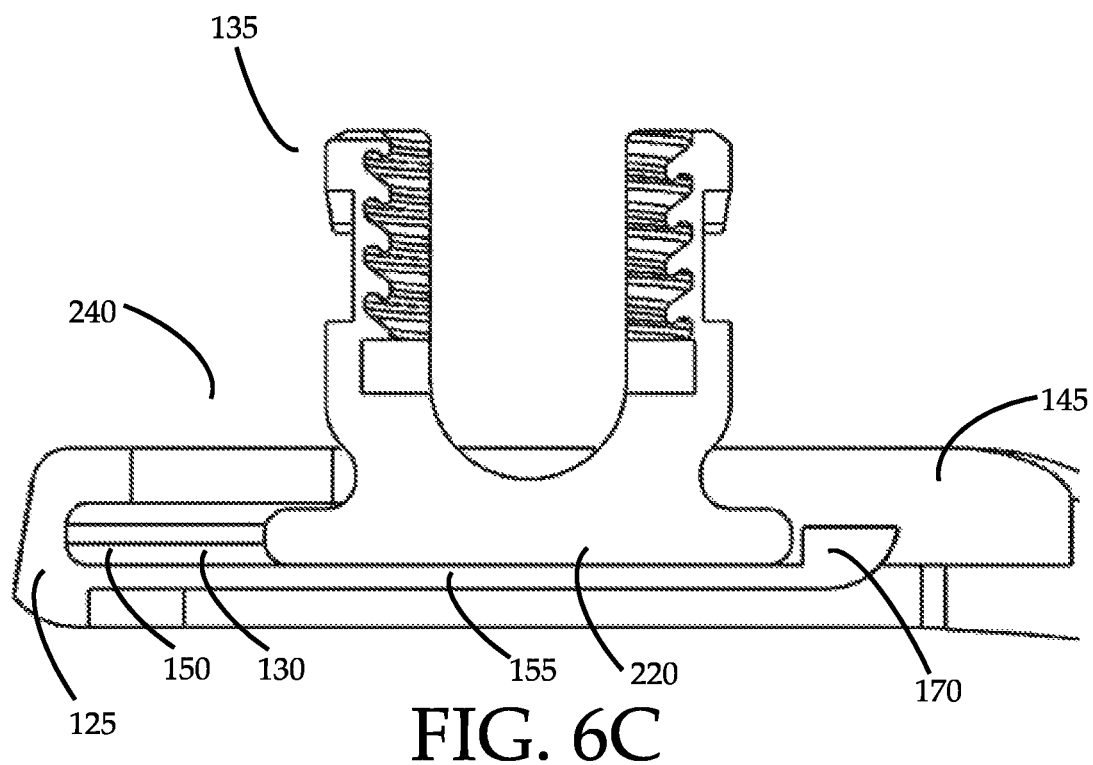
FIG. 6C is a section view illustrating a rod connector after having been inserted into an occipital plate according to the present disclosure.

FIGS. 6A-6C illustrate how rod connector 140 is to be inserted into or installed on occipital plate 100. Insertion of rod connector 135 may be accomplished in a similar method. Following the direction of the illustrated arrow 212 in FIG. 6A, base portion 200 is lowered into entry portion 145 of slot 130. The radius of base portion 200 is substantially the same as or smaller than the diameter of entry portion 145 so that base portion 200 can be pressed fully into slot 130. Removal of rod connecter 140 is similarly performed with base portion 220 positioned in entry portion 145.

FIG. 6B shows that when base portion 220 is pressed into entry portion 145 of slot 130, it depresses raised protrusion 170 of flex tab 155. Flex tab 155 normally occupies a neutral position but can be depressed so as to occupy a flexed position. With flex tab 155 depressed into the flexed position, base portion 200 can pass into holding portion 150 of slot 130 moving in the direction of the illustrated arrow. Holding portion 150 includes a flange 240 configured to mate with an edge of base portion 220 to not only retain base portion 220 in slot 130 but to also allow base portion 220 to rotate within slot 130 and translate medially and laterally along slot 130.

FIG. 6C shows that after insertion base portion 220 can be translated laterally in slot 130 from entry portion 145 into holding portion 150. When base portion 220 is translated laterally beyond the edge of raised protrusion 170, flex tab 155 pushes raised protrusion 170 upward or back into its neutral position. In the neutral position, raised protrusion 170 prevents base portion 220 from inadvertently backing out of slot 130. Rod connector 135 can be secured to extension 125 at any position in holding portion 150. In some embodiments, holding portion 150 is longer than shown in these illustrated embodiments.

FIGS. 7A-7C illustrate exemplary configurations of occipital plates having different locations of bend zones and varying angles of extensions 125. These figures also illustrate exemplary combinations that can be achieved using rod-to-rod connector 140 within occipital plate 100. FIG. 7A illustrates an occipital plate with a fixation plate portion 105 that, in this illustrated embodiment, includes five through-holes 110, three medial through-holes and two lateral through-holes. One bend zone is positioned on fixation plate portion 105, and one bend zone is at the connection point between fixation plate portion 105 and each of the two extensions 125. FIG. 7B illustrates an occipital plate with a fixation plate portion 105 that includes three medial through-holes and two lateral through-holes, with a bend zone at the connection point between fixation plate 105 and each of the two extensions 125. Bend zones in this exemplary configuration are also positioned between the medial through-holes and the lateral through-holes. FIG. 7C shows an exemplary embodiment of an occipital plate similar to FIG. 7B, but with the two extensions 125 at approximately 90 degrees to an imaginary line running from superior end 115 to inferior end 120.

Figure 8A:
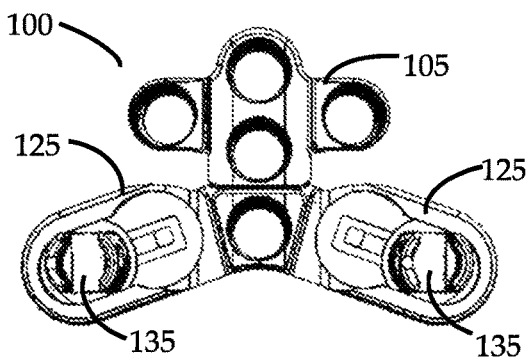
FIGS. 8A-8C illustrate various configurations of an occipital plate according to the present disclosure.
Figure 8B:
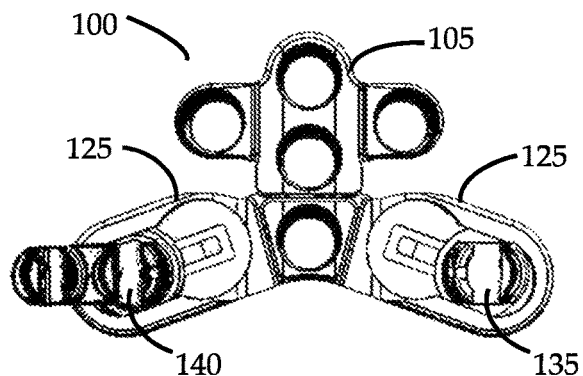
Figure 8C:
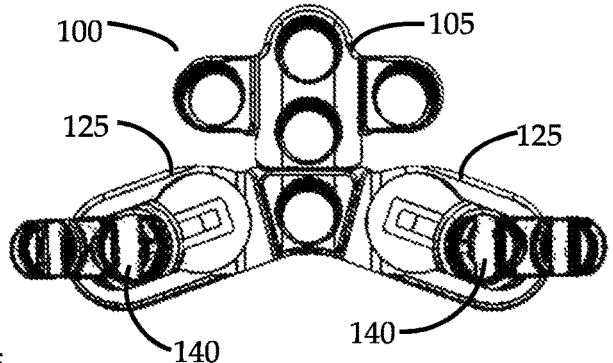

FIGS. 8A-8C illustrate the various combinations that can be achieved using rod connector 135 and/or rod-to-rod connector 140. FIG. 8A illustrates the use of two rod connectors 135 in each slot 130. This configuration allows for occipital plate 100 to be secured to up to two stabilization rods. FIG. 8B illustrates the use of one rod connector 135 in one slot 130 and one rod-to-rod connector 140 in the other slot 130. This configuration allows for occipital plate 100 to be secured to up to three stabilization rods. FIG. 8C illustrates the use of two rod-to-rod connectors 140 in each slot 130. This configuration allows for occipital plate 100 to be secured to up to four stabilization rods.

FIGS. 9A-9C illustrate one embodiment of a single rod connector 300 that, similar to rod connector 135, includes a base portion 310 and a body portion 320 that comprises two vertical side walls that are threaded on their respective interior surfaces so as to receive a set screw. Rod connector 300 is distinct from rod connector 135 in that base portion 310 includes two cut-outs or scalloped edges 330 that are, in this embodiment, positioned opposite each other.

FIGS. 9B and 9C illustrate the effect cut-outs 330 have on the overall shape of base portion 310. Cut-outs 330 are illustrated as positioned not only to be substantially opposite each other but also substantially parallel to the vertical walls of body portion 320. In some embodiments, cut-outs 330 are not parallel to the vertical walls of body portion 320. In some embodiments, cut-outs 330 are not positioned to be substantially opposite each other, and at least one cut-out 330 is not substantially parallel to the vertical walls of body portion 320.

Figure 10A:
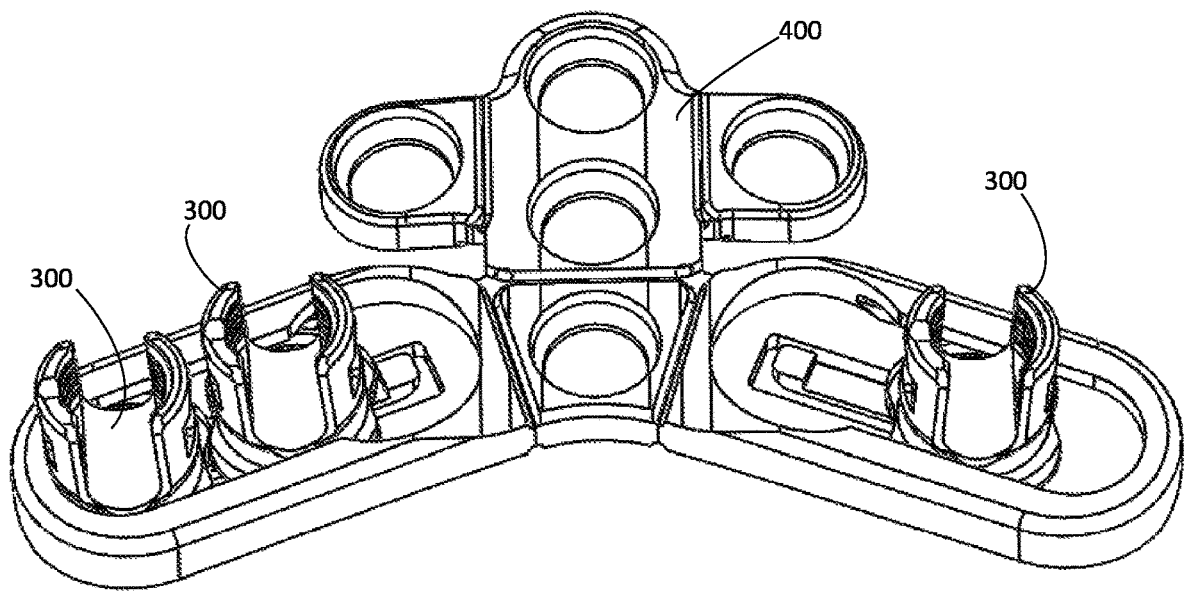
FIGS. 10A-10B illustrate an occipital plate according to the present disclosure that utilizes the rod connector shown in FIGS. 9A-9C.
Figure 10B:
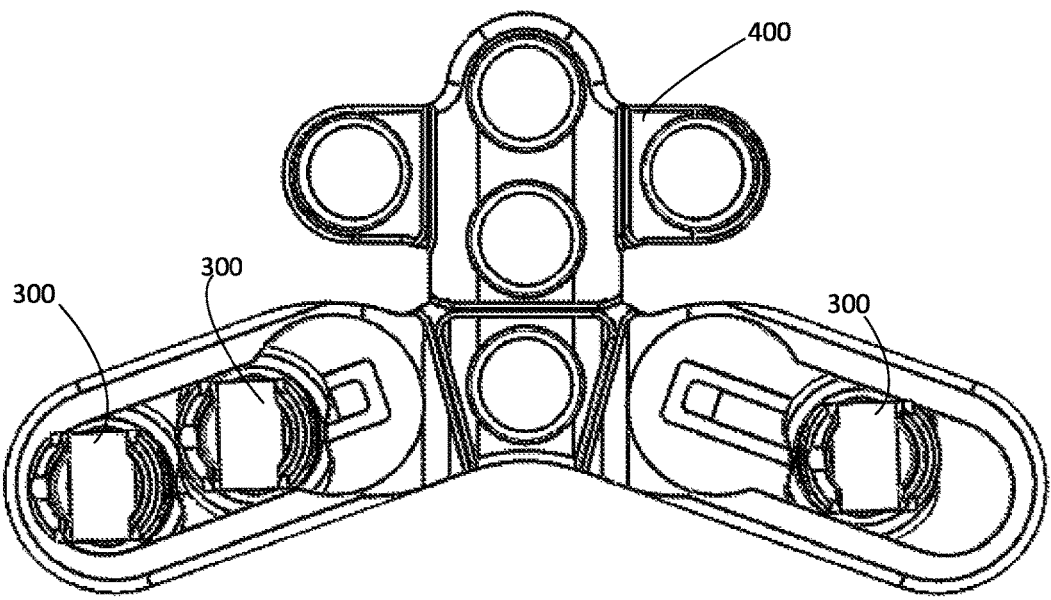

FIGS. 10A and 10B illustrate one advantage of rod connector 300 with its cut-outs 330, which is that two rod connectors 300 may more easily be inserted into a slot 430 of an occipital plate 400. Not only do cut-outs 330 allow rod connectors 300 to be placed closer together so as to both fit in slot 430, but the shape of cut-outs 330 accommodates the offset nature of rod connectors, i.e., the fact that when secured in place, each rod connector 300 may not be positioned orthogonally to the direction of slot 430. Such a configuration could allow for two rods to be connected to one side of occipital plate 400 while allowing for a slight angle variation between the two rods.

Although not illustrated, it is contemplated that a dual-rod connector, such as rod-to-rod connector 140, could also include one or more cut-outs, scalloped edges, or straight edges so as to fit both the dual-rod connector and another connector, which may itself be a dual-rod connector or a single-rod connector with one or more cut-outs, scalloped edges, or straight edges. Such configurations could allow for as many as three or even four rods to be secured to one side of an occipital plate while achieving some angular variation between the various rods.

Methods of using an occipital plate according to this disclosure include selecting type of connector to use in each slot. Moreover, because each slot includes a flex tab, one connector may be swapped out for a different connector quite simply either in situ or prior to implantation of the occipital plate on a patient's occiput. Methods of using an occipital plate may also include the step of selecting the type of occipital plate, including selecting an occipital plate that includes the desired number of through-holes, the desired angle and number of extensions, the desired number of bend zones, etc.

After the rod connector type and occipital plate type are selected, the rod connector may be inserted into a slot of the occipital plate. This may be done by first placing the base portion of the selected rod connector within an entry portion of the slot, and depressing a raised protrusion of the flex tab within the slot. The rod connector may then be translated laterally within the slot to engage with a holding portion of the slot. A lip or flange of the holding portion may assist in keeping the rod connector in place. Additionally, the raised protrusion may act as a retaining protrusion to prevent the rod connector base from sliding out of the slot.

EMBODIMENTS

The following embodiments are provided as examples only of specific configurations, materials, arrangements, etc. contemplated by the authors of this disclosure:

Embodiment 1

An occipital plate comprising:
a fixation plate portion having a superior end and an inferior end, the fixation plate portion comprising a plurality of through-holes; and
at least two extensions integrally connected to the fixation plate portion, the at least two extensions extending away from the fixation plate portion, each of the at least two extensions comprising:
  a rod connector comprising:
    a base having a protruding edge;
    at least two side walls extending from the base to define at least one U-shaped opening configured to receive at least one rod and at least one set screw;
  a slot for receiving the base of the rod connector, the slot having an entry portion and a holding portion, the holding portion having a first width and the entry portion having a second width that is greater than the first width, the holding portion having a flange extending at least partially along the perimeter of the lateral portion so as to engage with the protruding edge of the base; and
  a flex tab, at least a portion of the flex tab positioned at least partially in the entry portion such that, when deflected, the flex tab allows the base to be inserted into the entry portion and then slid into the holding portion.

Embodiment 2

The occipital plate of embodiment 1, wherein the plurality of through-holes comprises at least three midline through-holes comprising a superior through-hole, a middle through-hole, and an inferior through-hole, the at least three midline through-holes positioned along a first imaginary line running from the superior end to the inferior end of the fixation plate portion.

Embodiment 3

The occipital plate of embodiment 2, wherein the plurality of through-holes further comprises at least two lateral through-holes, each one positioned on either side of the midline through-holes.

Embodiment 4

The occipital plate of embodiment 2, wherein each of the at least two extensions extends in a direction substantially perpendicular to the first imaginary line of the fixation plate portion.

Embodiment 5

The occipital plate of embodiment 2, wherein the at least two extensions extend at an angle relative to the first imaginary line of the fixation plate portion, the angle being greater than about 90°, greater than about 95°, greater than about 100°, greater than about 105°, or greater than about 110°.

Embodiment 6

The occipital plate of embodiment 5, wherein each slot defines a second imaginary line that intersects the first imaginary line at about the inferior through-hole, at about the middle through-hole, at about a point between the respective centers of the middle and inferior through-holes, or at a point inferior to the center of the inferior through-hole.

Embodiment 7

The occipital plate of embodiment 1, 2, 3, 4, 5, or 6, wherein the flex tab comprises an arm having a proximal end secured to the extension and a distal end that is able to be deflected.

Embodiment 8

The occipital plate of embodiment 7, wherein the distal end of the arm comprises a retaining protrusion configured to prevent the base of the rod connector from sliding out of the slot.

Embodiment 9

The occipital plate of embodiment 1, 2, 3, 4, 5, 6, 7, or 8, wherein the plate further comprises bend zones positioned between the fixation plate portion and the extensions and/or between the middle through-hole and inferior through-hole.

Embodiment 10

The occipital plate of embodiment 1, 2, 3, 4, 5, 6, 7, or 8, wherein the plate further comprises a bend zone running from the superior end to the inferior end of the fixation plate portion on either side of the midline through-holes.

Embodiment 11

The occipital plate of embodiment 1, 2, 3, 4, 5, 6, 7, 8, 9, or 10, wherein the base of the rod connector is cylindrical in shape so as to be able to rotate within the slot.

Embodiment 12

The occipital plate of embodiment 1, 2, 3, 4, 5, 6, 7, 8, 9, 10, or 11, wherein at least one of the rod connectors is configured to receive a single stabilization rod.

Embodiment 13

The occipital plate of embodiment 12, wherein the base of the rod connector that is configured to receive a single stabilization rod includes at least one straight edge, scalloped edge, or cut-out.

Embodiment 14

The occipital plate of embodiment 13, further comprising at least a second rod connector that is configured to receive a single stabilization rod, wherein the base of the second rod connector includes at least one straight edge, scalloped edge, or cut-out, and wherein the first and second rod connectors are configured to be positioned in the same slot.

Embodiment 15

The occipital plate of embodiment 14, wherein each rod connector is able to be secured at an angle distinct from the other rod connector. Embodiment 16. The occipital plate of embodiment 14 or 15, wherein the second rod connector is configured to receive a single rod.

Embodiment 17

The occipital plate of embodiment 14 or 15, wherein the second rod connector is configured to receive two rods.

Embodiment 18

The occipital plate of embodiment 14, 15, 16, or 17, wherein the at least one straight edge, scalloped edge, or cut-out is substantially parallel to an axis defining the U-shaped opening.

Embodiment 19

The occipital plate of embodiment 14, 15, 16, or 17, wherein the at least one straight edge, scalloped edge, or cut-out is not parallel to an axis defining the U-shaped opening.

Embodiment 20

The occipital plate of embodiment 1, 2, 3, 4, 5, 6, 7, 8, 9, 10, 11, 12, 13, 14, 15, 16, 17, 18, or 19, wherein at least one of the rod connectors is configured to receive two stabilization rods.

Embodiment 21

The occipital plate of embodiment 20, wherein the at least one rod connector configured to receive two stabilization rods comprises three side walls-a first and a second wall defining a first U-shaped opening and a third wall defining, with the second wall, a second U-shaped opening.

Embodiment 22

The occipital plate of embodiment 21, wherein the second U-shaped opening is raised relative to the first U-shaped opening.

Embodiment 23

The occipital plate of embodiment 21 or 22, wherein an imaginary line between the respective centers of the first and second U-shaped openings is not orthogonal to an axis of the first U-shaped opening.

Embodiment 24

The occipital plate of embodiment 1, 2, 3, 4, 5, 6, 7, 8, 9, 10, 11, 12, 13, 14, 15, 16, 17, 18, 19, 20, 21, 22, 23, wherein the rod connector is removable.

Embodiment 25

An occipital plate system comprising:
- the occipital plate of embodiment 1, 2, 3, 4, 5, 6, 7, 8, 9, 10, 11, 12, 13, 14, 15, 16, 17, 18, 19, 20, 21, 22, 23, or 24;
- a plurality of fixation screws, each one configured to be inserted through the plurality of through-holes, respectively, of the occipital plate; and
- two or more fixation rods received in the U-shaped openings of the rod connectors;
- wherein each fixation screw comprises a threaded shank and a head, the head having a larger diameter than the threaded shank, and at least a portion of the head having a larger diameter than a diameter of at least a portion of the through-holes.

Embodiment 26

A method of implanting an occipital plate, the method comprising:
- positioning the plate of embodiment 1, 2, 3, 4, 5, 6, 7, 8, 9, 10, 11, 12, 13, 14, 15, 16, 17, 18, 19, 20, 21, 22, 23, or 24 on the occiput of a patient's cranium;
- inserting a fixation screw through each through-hole of the occipital plate and into the patient's cranium;
- inserting each rod connector into the respective slots;
- positioning each rod connector as desired;
- placing one or more rods in each rod connector; and
- placing set screws in each rod connector to secure each of the rods in place and to secure each rod connector in place in each slot.

Embodiment 27

The method of embodiment 26, further comprising inserting at least one additional rod connector into at least one of the respective slots.

Embodiment 28

The method of embodiment 27, wherein the at least one additional rod connector is able to be secured in a non-parallel orientation relative to the other rod connector in the same slot.

Embodiment 29

The method of embodiment 27 or 28, wherein a base portion of the additional rod connector includes one or more straight edges, scalloped edges, or cut-outs.

Embodiment 30

The method of embodiment 27 or 28, wherein the additional rod connector is configured to receive a single rod.

Embodiment 31

The method of embodiment 27 or 28, wherein the additional rod connector is configured to receive two rods.

Embodiment 32

The method of embodiment 26, 27, 28, 29, 30, or 31, further comprising pre-bending the plate prior to positioning the plate on the occiput.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In some embodiments, the terms "about" and "approximately" refer to numerical parameters within 10% of the indicated range.

The terms "a," "an," "the," and similar referents used in the context of describing the embodiments of the present disclosure (especially in the context of any claimed invention) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the disclosed embodiments. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to the embodiments precisely as shown and described.

The invention claimed is:
1. An occipital plate comprising:
 a fixation plate portion having a first bone contacting surface configured to contact an occiput, a superior end and an inferior end, the fixation plate portion comprising a plurality of through-holes extending through the first bone contacting surface; and
 at least two extensions integrally connected to the fixation plate portion, the at least two extensions extending away from the fixation plate portion, each of the at least two extensions comprising:

a second bone contacting surface configured to contact the occiput;
a first rod connector comprising:
   a base having a protruding edge; and
   at least two side walls extending from the base to define at least one U-shaped opening configured to receive at least one rod and at least one set screw;
a slot extending through the second bone contacting surface for receiving the base of the first rod connector, the slot having an entry portion and a holding portion, the holding portion having a first width and the entry portion having a second width that is greater than the first width, the holding portion having a flange extending at least partially along a perimeter of the holding portion so as to engage with the protruding edge of the base; and
a flex tab extending within the slot and comprising a proximal end integrally connected to a portion of the holding portion and a distal end having a retaining protrusion positioned at least partially in the entry portion such that, when deflected from an initial position, the flex tab allows the base to be inserted into the entry portion and then slid into the holding portion, and when returned back to the initial position, prevent the first rod connector from sliding out of the slot;
wherein the plurality of through-holes comprises at least three midline through-holes comprising a superior through-hole, a middle through-hole, and an inferior through-hole, the at least three midline through-holes positioned along a first imaginary line running from the superior end to the inferior end of the fixation plate portion; and
wherein the at least two extensions extend at an angle relative to the first imaginary line of the fixation plate portion, the angle being greater than about 95°.

2. The occipital plate of claim 1, wherein the plate further comprises bend zones positioned between the fixation plate portion and the at least two extensions and/or between the middle through-hole and inferior through-hole.

3. The occipital plate of claim 1, wherein the plate further comprises a bend zone running from the superior end to the inferior end of the fixation plate portion on either side of the midline through-holes.

4. The occipital plate of claim 1, wherein the base of the first rod connector is cylindrical in shape so as to be able to rotate within the slot.

5. The occipital plate of claim 1, wherein the first rod connector is configured to receive a single stabilization rod.

6. The occipital plate of claim 5, wherein the base of the first rod connector includes at least one straight edge, scalloped edge, or cut-out.

7. The occipital plate of claim 6, further comprising a second rod connector comprising
   a base having a protruding edge; and
   at least two side walls extending from the base to define at least one U-shaped opening configured to receive at least one rod and at least one set screw;
   wherein the base of the second rod connector includes at least one straight edge, scalloped edge, or cut-out, and wherein the first and second rod connectors are configured to be positioned in the same slot.

8. The occipital plate of claim 7, wherein each rod connector is able to be secured at an angle distinct from the other rod connector.

9. The occipital plate of claim 7, wherein the second rod connector is configured to receive two rods.

10. The occipital plate of claim 7, wherein the at least one straight edge, scalloped edge, or cut-out is substantially parallel to an axis defining the at least one U-shaped opening of the second rod connector.

11. The occipital plate of claim 7, wherein the at least one straight edge, scalloped edge, or cut-out is not parallel to an axis defining the at least one U-shaped opening of the second rod connector.

12. The occipital plate of claim 1, wherein the first rod connector is configured to receive two stabilization rods.

13. The occipital plate of claim 12, wherein the at least two side walls of the first rod connector comprises three side walls, a first and a second of the three side walls defining a first U-shaped opening of the at least one U-shaped opening and a third of the three side walls defining, with the second side wall, a second U-shaped opening of the at least one U-shaped opening.

14. The occipital plate of claim 13, wherein the second U-shaped opening is raised relative to the first U-shaped opening.

15. The occipital plate of claim 13, wherein an imaginary line between the respective centers of the first and second U-shaped openings is not orthogonal to an axis of the first U-shaped opening.

16. The occipital plate of claim 1, wherein the first rod connector is removable.

* * * * *